United States Patent
Han et al.

(10) Patent No.: US 11,718,823 B2
(45) Date of Patent: Aug. 8, 2023

(54) METHODS AND MATERIALS FOR RAPID PREPARATION OF 3D SPHEROIDS/ORGANOIDS

(71) Applicant: Purdue Research Foundation, West Lafayette, IN (US)

(72) Inventors: Bumsoo Han, West Lafayette, IN (US); George Tsu-Chih Chiu, West Lafayette, IN (US); Cih Cheng, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 157 days.

(21) Appl. No.: 17/108,009

(22) Filed: Dec. 1, 2020

(65) Prior Publication Data

US 2021/0238541 A1    Aug. 5, 2021

Related U.S. Application Data

(60) Provisional application No. 62/969,177, filed on Feb. 3, 2020.

(51) Int. Cl.
| | | |
|---|---|---|
| *B33Y 10/00* | (2015.01) | |
| *B33Y 70/00* | (2020.01) | |
| *C12N 5/00* | (2006.01) | |
| *C12N 5/0775* | (2010.01) | |
| *C12N 5/071* | (2010.01) | |
| *C12N 5/09* | (2010.01) | |

(52) U.S. Cl.
CPC .......... *C12N 5/0062* (2013.01); *B33Y 10/00* (2014.12); *B33Y 70/00* (2014.12); *C12N 5/0663* (2013.01); *C12N 5/0693* (2013.01); *C12N 5/0697* (2013.01); *C12N 2513/00* (2013.01)

(58) Field of Classification Search
CPC ..... C12N 5/0062; C12N 5/0697; B33Y 10/00
See application file for complete search history.

(56) References Cited

U.S. PATENT DOCUMENTS 10,676,712 B2    6/2020    O'Mahony et al.

FOREIGN PATENT DOCUMENTS

WO    WO-2013192290 A1 *    12/2013    ............... A61F 2/08

OTHER PUBLICATIONS

Kim et al. Directed fusion of cardiac spheroids into larger heterocellular microtissues enables investigation of cardiac action potential propagation via cardiac fibroblasts. PLoS One 2018, 13(5):e0196714. (Year: 2018).*
Negro, A., et al., 3D Inkjet Printing of Complex, Cell-Laden Hydrogel Structures, Scientific Reports, (2018) 8:17099.
Ling, K., et al., Bioprinting-Based High-Throughput Fabrication of Three-Dimensional MCF-7 Human Breast Cancer Cellular Spheroids, Engineering vol. 1, Issue 2, Jun. 2015, pp. 269-274.
Li, Y., et al., Hydrogel microenvironments for cancer spheroid growth and drug screening, Sci. Adv. 2018; 4 : eaas8998.
Robu, Au, et al., Using Sacrificial Cell Spheroids for the Bioprinting of Perfusable 3D Tissue and Organ Constructs: A Computational Study, Computational and Mathematical Methods in Medicine 2019(3):1-9.

* cited by examiner

*Primary Examiner* — Allison M Fox
*Assistant Examiner* — Jennifer S Spence
(74) *Attorney, Agent, or Firm* — Purdue Research Foundation

(57) ABSTRACT

The present disclosure relates to a novel method for rapid preparation of three dimensional (3D) spheroids/organoids, and the 3D spheroids/organoids prepared by the novel method.

6 Claims, 5 Drawing Sheets
(4 of 5 Drawing Sheet(s) Filed in Color)

METHODS AND MATERIALS FOR RAPID PREPARATION OF 3D SPHEROIDS/ORGANOIDS

CROSS-REFERENCE TO RELATED APPLICATION

This application claims the priority benefit of U.S. Provisional Patent application No. 62/969,177, filed Feb. 3, 2020, which is incorporated herein by reference in its entirety.

GOVERNMENT RIGHTS

This invention was made with government support under CMMI-1449358 awarded by the National Science Foundation. The government has certain rights in the invention.

TECHNICAL FIELD

The present disclosure relates to a novel method for rapid preparation of three dimensional (3D) spheroids/organoids, and the 3D spheroids/organoids prepared by the novel method.

BACKGROUND

This section introduces aspects that may help facilitate a better understanding of the disclosure. Accordingly, these statements are to be read in this light and are not to be understood as admissions about what is or is not prior art.

Multicellular spheroids are three-dimensional cellular aggregates and one of the most common and versatile way to culture cells in 3D. Spheroid cultures emerged since three-dimensional (3D) cell culture systems have become powerful tools with the capability of recapitulating not only the in vivo morphology, but the cell connectivity, polarity, gene expression, and tissue architecture. Spheroids are typically formed using pellet culture, liquid overlay, hanging drop, spinning flask, and magnetic levitation methods. However, these conventional methods lack reproducibility and wide distribution of spheroid sizes. Recently, more advanced microfabrication techniques have been proposed to address these limitations. Microfabrication to form concave hydrogel microwell arrays has shown the potential to generate uniform-sized multicellular spheroids. Microfluidic platforms are a more sophisticated method, which facilitates the generation of larger, more complex spheroids and allows for long-term studies since the parameters of their microenvironment can be tightly controlled. Alternatively, encapsulation of cells into a hydrogel to form the cell spheroids can achieve a higher level of control over cell-cell interactions. The spheroid size and functionality could be further modulated by the stiffness of the encapsulating hydrogel. Despite these contributions, challenges still remain. Since current 3D culture methodologies are diverse, resulting in spheroids that vary in terms of size, morphology, and complexity. This leads to challenges in obtaining standards with respect to the assay protocols and output data for any given cell type. Except for the reproducibility and the spheroid size uniformity, effort is still needed to establish a standardized and validated 3D cell model. Another critical issue is the growth rate of the cell spheroids. It normally takes more than a week to achieve the spheroid size larger than 500 µm, as shown in FIG. 1. See A. P. Andersen, M. Flinck, E. K. Oernbo, N. B. Pedersen, B. M. Viuff, and S. F. Pedersen, "Roles of acid-extruding ion transporters in regulation of breast cancer cell growth in a 3-dimensional microenvironment," Mol. Cancer, vol. 15, no. 1, pp. 1-18, 2016. This slow production rate will impede the progress of the spheroid culture system.

Therefore, novel methods for rapid preparation of 3D spheroids/organoids are still needed.

SUMMARY

The present disclosure relates to a novel method for rapid preparation of 3D spheroids/organoids, and the 3D spheroids/organoids prepared by the novel method.

In one embodiment, the present disclosure provides a method of printing a cellular spheroid with a shell and a core, wherein the method comprises:

providing a first solution comprising a first hydrogel, a first collagen, and a plurality of first cells, wherein the first cells are configured to substantially stay in the shell of said cellular spheroid;

providing a second solution comprising a second hydrogel, a second collagen, and a plurality of second cells; wherein the second cells are configured to substantially stay in the core of said cellular spheroid;

printing said first solution on a substrate and incubate said first solution for gelation;

printing said second solution on said substrate and incubate said second solution for gelation, wherein the incubated first solution is adjacent to the incubated second solution; and adding a cell culture medium to the incubated first solution and the incubated second solution to allow the incubated first solution and the incubated second solution to form a cellular spheroid and grown to a desired size, wherein the first hydrogel and the second hydrogel may be same or different, wherein the first collagen and the second collagen may be same or different, wherein the first cell and the second cell are different, wherein the first cell has higher contractility than the second cell.

BRIEF DESCRIPTION OF THE DRAWINGS

The patent or application file contains at least one drawing executed in color. Copies of this patent or patent application with color drawings(s) will be provided by the Office upon request and payment of the necessary fee.

DETAILED DESCRIPTION

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "hydrogel" may refer to a network of physically or chemically cross-linked polymer molecules that is inflated with an aqueous medium. Any natural or synthetic hydrogel may be used as far as it can provide necessary environment for spheroid grow purposes.

Figure 1:
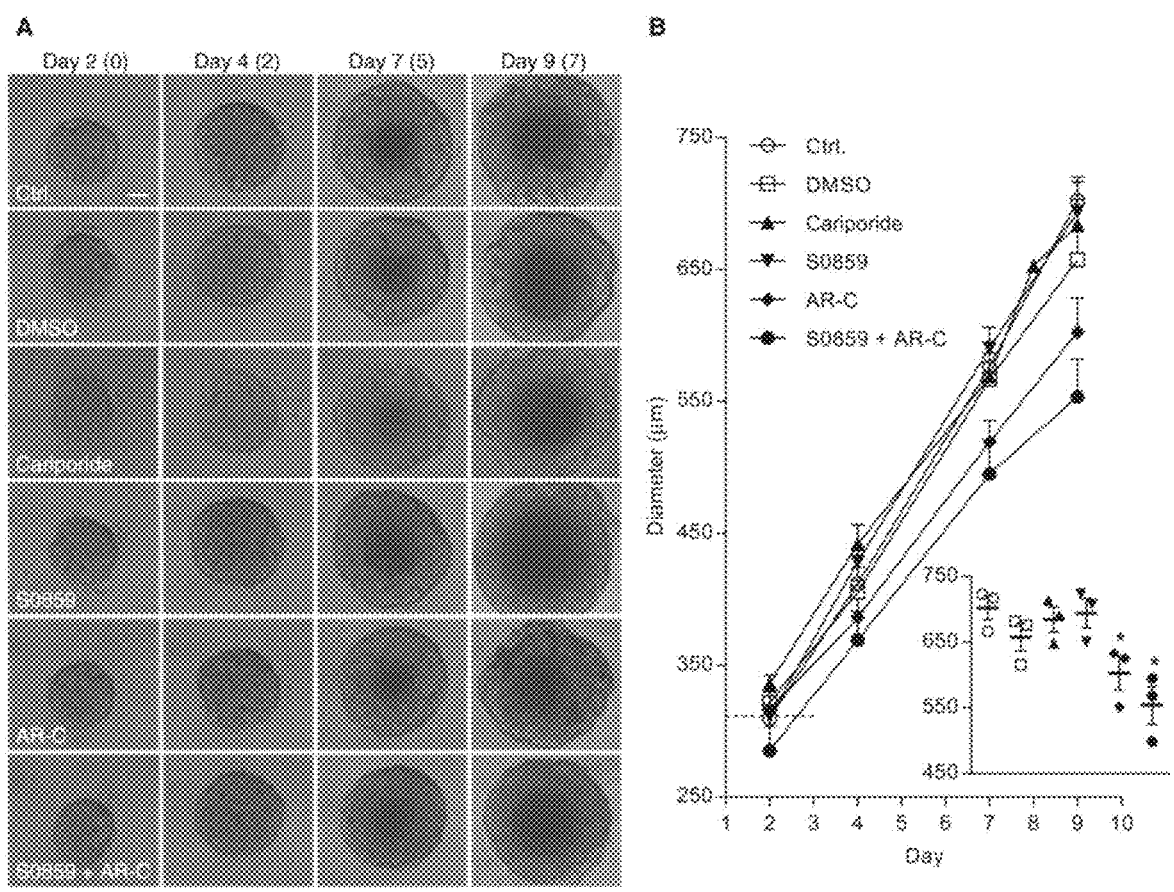
FIG. 1 illustrates 3D spheroids/organoids made by prior art method that it takes more than a week to achieve a spheroid size larger than 500 µm.
Figure 2:
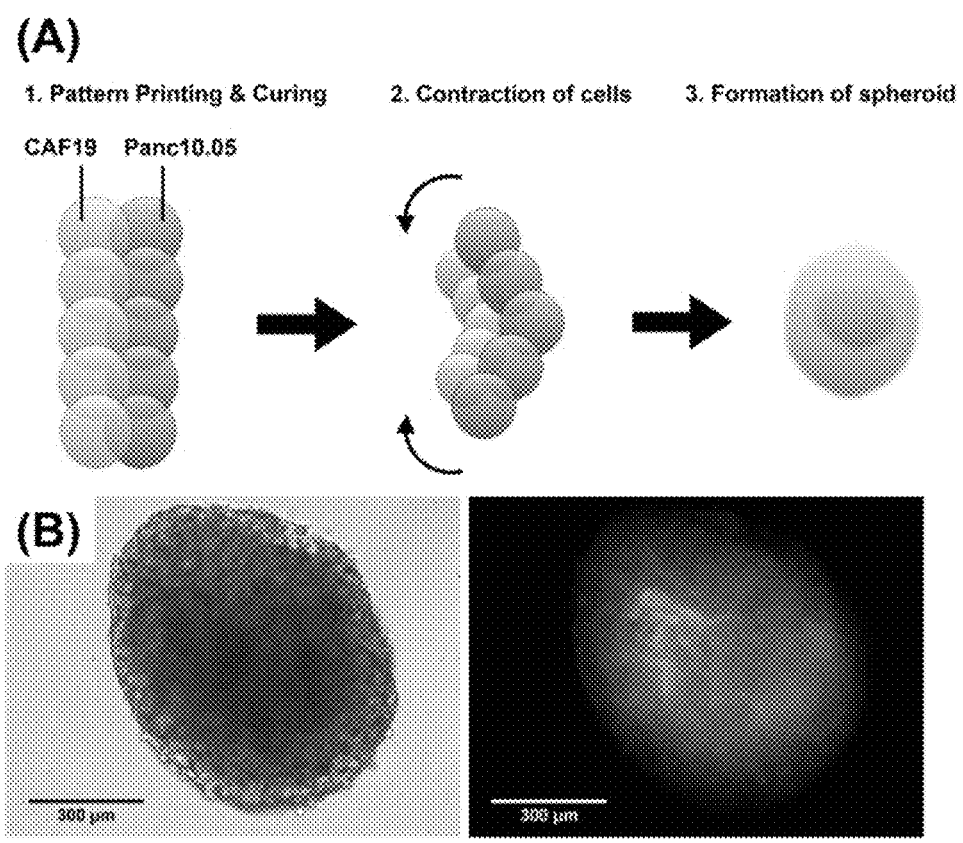
FIG. 2 illustrates fabrication of multicellular spheroid by digital hydrogel printing. (A) Procedure schematics of multicellular spheroid fabrication. (B) Bright-field and fluorescence images of a spheroid formed by cells-laden hydrogel printing (after culturing for 1 day).

In the present disclosure, a concept of the fabrication of multicellular spheroids by digital hydrogel printing is demonstrated. The process is shown in FIG. 2. First, two overlapped arrays of hydrogel drops are printed on a glass slide chamber, which loaded with two different types of cells: pancreatic adenocarcinoma epithelial cells transfected with red fluorescence protein (Panc10.05), and stromal cells with green fluorescence protein (CAF19). The hydrogel (P(PF407)) is further mixed with type I collagen to enhance the strength of the matrix while maintaining the printability. Then the printed patterns would be placed in an incubator for curing. After the gelation, a medium is added to and keep culturing the matrix. Finally, the spheroid would be formed within approximately 12 hours, with the CAF19 surrounded with Panc10.05. The underlying mechanism is said to be the difference in contractility between these two cells. The CAF19 are more contractile than the Panc10.05, which makes the gelled pattern shrink toward the direction of CAF19 (FIG. 2A). The spheroid with the size of ~0.5 μm is formed in a short time (<1 day), as shown in FIG. 2B.

Materials and Methods
Cells Culture and Reagents

Human pancreatic cancer cells (Panc10.05) and pancreatic cancer associated fibroblast (CAF19) are used. Panc10.05 and CAF19 are cultured in Dulbecco's Modified Eagle Medium (Advanced DMEM) supplemented with 10% v/v fetal bovine serum (FBS), 2 mM L-glutamine (L-glu), and 100 μg ml$^{-1}$ penicillin/streptomycin (P/S). All cells are cultured in 25 cm$^2$ T-flask at 37° C. and 5% $CO_2$. Cells are harvested for the experiments using 0.05% trypsin and 0.53 mM EDTA when the cells reached 70-80% confluency.

Preparation of Cell-Laden Hydrogel Solutions

For the polymer matrix, the inverse thermogel poly(N-isopropyl acrylamide-co-methyl methacrylate) (P(NIPAM-AM)) and rat tail collagen type-1 are selected. The P(NIPAM-AM) is dissolved in deionized water at 4° C. to achieve 1% w/v concentration. A stock solution of rat tail collagen type-1 is mixed with 10×PBS, 1 N NaOH, 0.1 M HEPE solution, 5% v/v FBS, 2 mM L-glu, 100 μg ml$^{-1}$ P/S, and cell-culture grade distilled water at appropriate proportions to obtain a final collagen solution that had neutral pH, isotonic ionic strength, and a collagen concentration of 3 mg ml$^{-1}$. The collagen-based hydrogel solution is obtained by mixing 3 mg ml$^{-1}$ collagen solution with 1% w/v P(NIPAM-AM) solution with 3:1 volume-to-volume ratio. Finally, the cell-laden inks for cell printing experiments are prepared by mixing the collagen-based hydrogel solution with harvested Panc10.05 and CAF19 cells, respectively.

Printer Setup

The drop-on-demand (DOD) printing setup consists of a PipeJet® dispenser and a stage controller. The PipeJet® dispenser is driven by a specific high-voltage pulse generated by the control electronics. A piezo stack actuator will partially squeeze the tube installed in the dispenser. Due to the implied volume displacement, the liquid is ejected out of the orifice of the tube. An XY stage provides a substrate movement with 0.2 μm addressability. The prepared inks would be loaded into the ink reservoir, which is connected to a nozzle with 500 μm diameter.

3D Printing of Cell Spheroid

The process is illustrated in FIG. 2A. Firstly, five drops containing Panc10.05 were deposited on a glass well-plate to form a line array. Then, the well-plate was placed in an incubator for 3 minutes for the gelation of the polymer matrix. Next, the other five drops containing CAF19 were deposited on the glass well-plate to form a line array adjacent to the first line. Again, the well-plate was placed in the incubator for 3 minutes for the gelation of the polymer matrix. After printing and curing, we added the medium into the well and placed the well-plate in an incubation stage for time-lapse imaging. The behavior of the cell-containing construct was recorded. After adding the medium, the matrix would detach from the glass surface and start to shrink and form a spheroid due to the contraction force of cells. Because of the contractility difference between CAF19 and Panc10.05 (CAF19 has a strong contraction force while Panc10.05 is less contractile), the cell spheroid would be formed with the CAF19 at the center surrounded by the Panc10.05, as shown in FIG. 2B.

Figure 3:
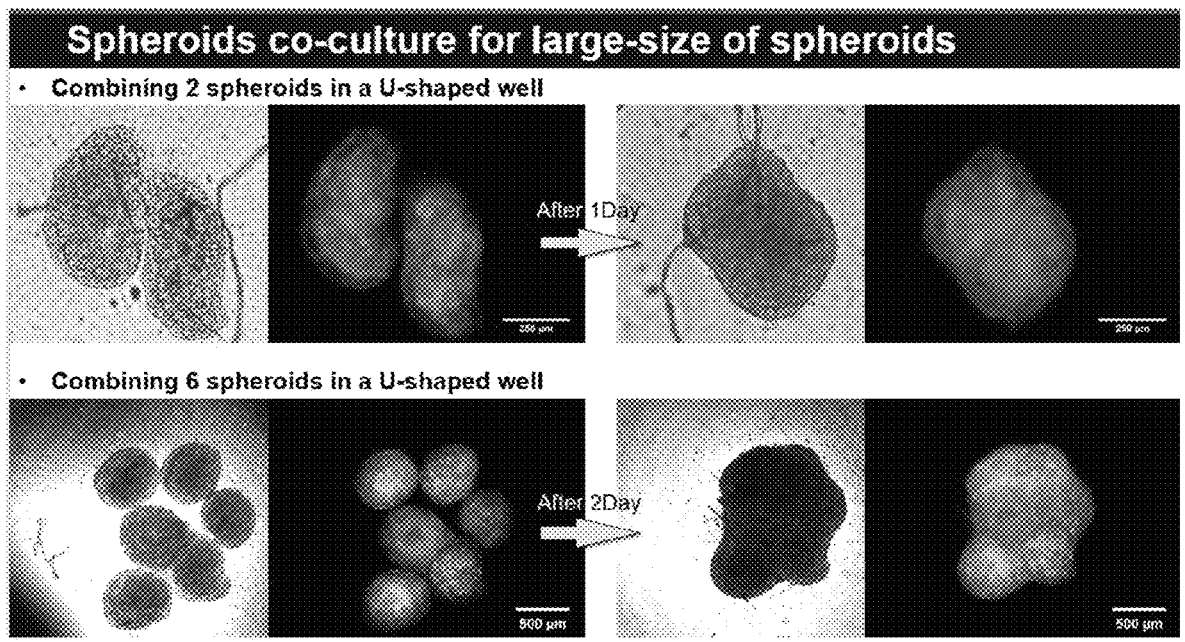
FIG. 3 illustrates larger spheroids formation by combining a plurality of 3D spheroids/organoids made by the printing method of the present disclosure.

3D spheroids prepared with the printing method of this disclosure can be co-cultured together to further speed up the culturing process to lead to larger spheroids, as shown in FIG. 3.

Figure 4:
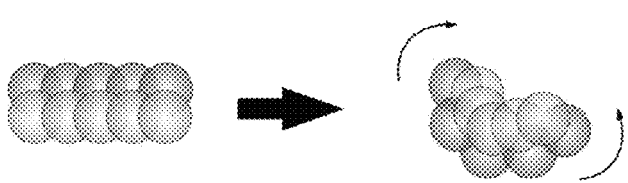
FIG. 4 illustrates factors that may impact the folding process of the printed spheroids.
Figure 5:
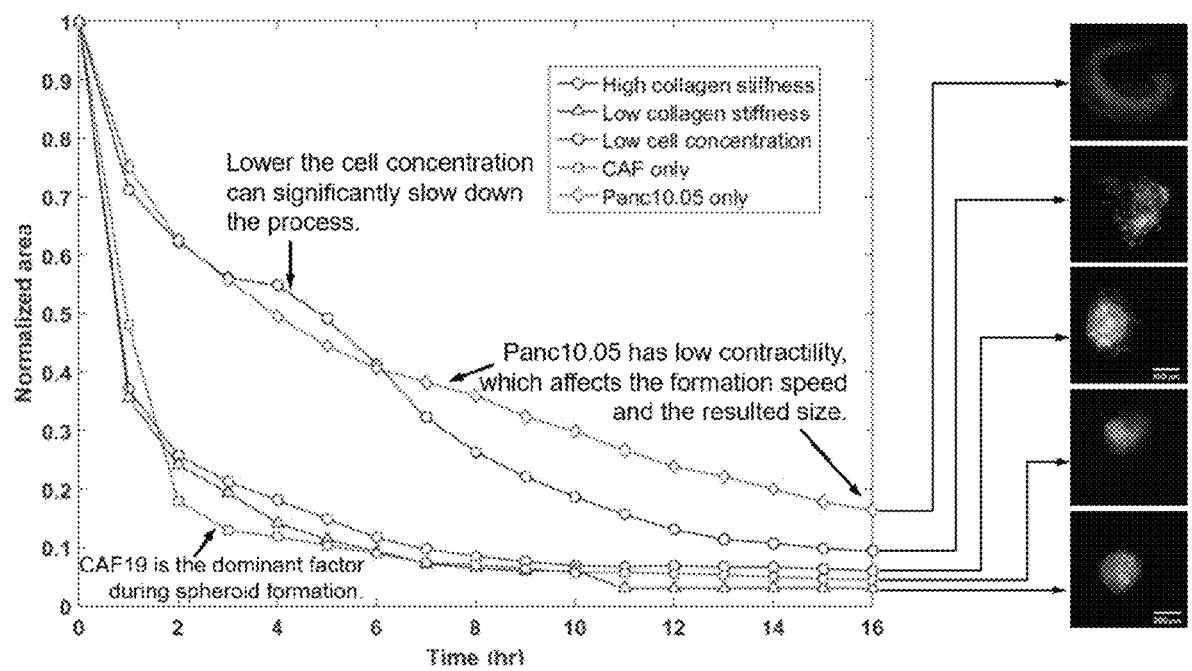
FIG. 5 illustrates data that shows the factors that impact the folding process of the printed spheroids.

Through the extensive studies, it has been found that certain factors may impact the folding/forming process of the 3D spheroids, as shown in FIG. 4 and FIG. 5. The contraction force of the cells triggers the shrinkage of the printed matrix. Cell type appears to be the dominant factor (CAF19 is more contractile than Panc10.05). Cell concentration is also a significant factor. However, the cells will eventually form the spheroids with similar configuration (spherical shape) and size either by changing the matrix stiffness or by changing the cell concentration.

In one embodiment, the present disclosure provides a method of printing a cellular spheroid with a shell and a core, wherein the method comprises:

providing a first solution comprising a first hydrogel, a first collagen, and a plurality of first cells, wherein the first cells are configured to substantially stay in the shell of said cellular spheroid;

providing a second solution comprising a second hydrogel, a second collagen, and a plurality of second cells; wherein the second cells are configured to substantially stay in the core of said cellular spheroid;

printing said first solution on a substrate and incubate said first solution for gelation; and printing said second solution on said substrate and incubate said second solution for gelation, wherein the incubated first solution is adjacent to the incubated second solution, adding a cell culture medium to the incubated first solution and the incubated second solution to allow the incubated first solution and the incubated second solution to form a cellular spheroid and grown to a desired size, wherein the first hydrogel and the second hydrogel may be same or different, wherein the first collagen and the second collagen may be same or different, wherein the first cell and the second cell are different, wherein the first cell has higher contractility than the second cell.

In one embodiment regarding the method of printing a cellular spheroid, wherein the printing and the gelation of the second solution is carried out after printing and the gelation of the first printed solution.

In one embodiment regarding the method of printing a cellular spheroid, wherein the first hydrogel and the second hydrogel are same, and wherein the first collagen and the second collagen are same.

In one embodiment regarding the method of printing a cellular spheroid, wherein either the first solution or the second solution can be printed first. There is no specific requirement for the order of printing, as far as the printed and cured solutions are adjacent to each other.

In one embodiment regarding the method of printing a cellular spheroid, wherein the cellular spheroid can be formed within 12 hours.

In one embodiment regarding the method of printing a cellular spheroid, wherein a cellular spheroid with a diameter of about 0.5 µm can be formed within 24 hours.

In one embodiment regarding the method of printing a cellular spheroid, wherein a plurality of formed cellular spheroids can be co-cultured together to form larger cellular spheroid more quickly.

In one embodiment regarding the method of printing a cellular spheroid, wherein size and shape of the formed cellular spheroid can be controlled by different cells with different contraction forces.

In one embodiment regarding the method of printing a cellular spheroid, wherein size and shape of the formed cellular spheroid can be controlled by different cell concentrations.

In one embodiment regarding the method of printing a cellular spheroid, wherein size and shape of the formed cellular spheroid can be controlled by different collagen stiffnesses.

In one embodiment regarding the method of printing a cellular spheroid, wherein said cells can be any kind of cancer cells.

Those skilled in the art will recognize that numerous modifications can be made to the specific implementations described above. The implementations should not be limited to the particular limitations described. Other implementations may be possible.

We claim:

1. A method of printing a cellular spheroid with a shell and a core, wherein the method comprises:
    providing a first solution comprising a first hydrogel, a first collagen, and a plurality of first cells, wherein the first cells are configured to substantially stay in the shell of said cellular spheroid;
    providing a second solution comprising a second hydrogel, a second collagen, and a plurality of second cells; wherein the second cells are configured to substantially stay in the core of said cellular spheroid;
    wherein the first hydrogel and the second hydrogel may be same or different, wherein the first collagen and the second collagen may be same or different, wherein the first cells and the second cells are different, wherein the second cells have higher contractility than the first cells;
    printing a plurality of droplets of the first solution on a substrate and incubating said first solution for gelation to form a first line array;
    printing a plurality of droplets of the second solution on said substrate adjacent to the first line array and incubating said second solution for gelation to form a second line array, wherein the printing and the gelation of the second solution is carried out after the printing and the gelation of the first printed solution, wherein the incubated first solution first line array is adjacent to the incubated second solution second line array, thereby forming a cell-containing construct;
    adding a cell culture medium to the cell-containing construct incubated first solution and the incubated second solution to allow the cell-containing construct incubated first solution and the incubated second solution to detach from the substrate and to shrink towards the direction of the second cells, which forms thereby forming a cellular spheroid with a shell and a core, wherein the shell comprises the first cells, and the core comprises the second cells; and
    growing the cellular spheroid to a desired size, wherein the shell comprises the first cells, and the core comprises the second cells.

2. The method of claim 1, wherein the first hydrogel and the second hydrogel are same, and wherein the first collagen and the second collagen are same.

3. The method of claim 1, wherein a cellular spheroid with a diameter of about 500 µm can be formed within 24 hours.

4. The method of claim 3, wherein a plurality of formed cellular spheroids can be co-cultured together to form a larger cellular spheroid.

5. The method of claim 3, wherein size and shape of the formed cellular spheroid can be controlled by different cells with different contraction forces.

6. The method of claim 3, wherein size and shape of the formed cellular spheroid can be controlled by different cells with different cell concentrations or different collagen stiffnesses.

* * * * *